United States Patent
Guinn et al.

(10) Patent No.: US 7,176,315 B2
(45) Date of Patent: Feb. 13, 2007

(54) ENANTIOMERS OF 6-[(4-CHLORO-PHENYL)-HYDROXY-(3-METHYL-3H-IMIDAZOL-4-YL)-METHYL]-4-[3-(3-HYDROXY-3-METHYL-BUT-1-YNYL)-PHENYL]-1-METHYL-1H-QUINOLIN-2-ONE AND SALTS THEREOF, USEFUL IN THE TREATMENT OF CANCER

(75) Inventors: R. Mark Guinn, Mystic, CT (US); Subramanian Sam Guhan, Niantic, CT (US); Karl K Ng, Warwick, RI (US); Derek L. Tickner, Waterford, CT (US); Marcus Douglas Ewing, Putnam, CT (US); Clifford N. Meltz, Niantic, CT (US); Bryan Li, East Lyme, CT (US); Kees Pouwer, Groningen (NL)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/824,034

(22) Filed: Apr. 14, 2004

(65) Prior Publication Data

US 2004/0192727 A1    Sep. 30, 2004

Related U.S. Application Data

(62) Division of application No. 10/228,657, filed on Aug. 27, 2002, now Pat. No. 6,740,757.

(60) Provisional application No. 60/315,740, filed on Aug. 29, 2001.

(51) Int. Cl.
    C07D 215/16    (2006.01)
(52) U.S. Cl. .................................................... 546/157
(58) Field of Classification Search ................. 546/157
    See application file for complete search history.

(56) References Cited

U.S. PATENT DOCUMENTS

| | | | |
|---|---|---|---|
| 5,747,498 A | 5/1998 | Schnur et al. | |
| 5,968,952 A | 10/1999 | Venet et al. | |
| 6,037,350 A | 3/2000 | Venet et al. | |
| 6,040,334 A | 3/2000 | Myers et al. | |
| 6,071,935 A | 6/2000 | Lyssikatos | |
| 6,083,985 A | 7/2000 | Yonemoto et al. | |
| 6,150,377 A | 11/2000 | Lyssikatos et al. | |
| 6,444,854 B1 * | 9/2002 | Dapremont et al. | 568/314 |
| 6,740,757 B2 * | 5/2004 | Guinn et al. | 546/157 |

FOREIGN PATENT DOCUMENTS

| | | |
|---|---|---|
| EP | 0856315 A1 | 8/1996 |
| WO | 9705902 | 2/1997 |
| WO | 9716443 | 5/1997 |
| WO | 9721701 | 6/1997 |
| WO | 9857633 | 12/1998 |
| WO | 0016778 | 3/2000 |

* cited by examiner

*Primary Examiner*—D. Margaret Seaman
(74) *Attorney, Agent, or Firm*—Steve T. Zelson; Christian M. Smolizza

(57) ABSTRACT

This invention relates to the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, prodrugs thereof, and pharmaceutically acceptable salts and solvates of said compounds and said prodrugs, that are useful in the treatment of hyperproliferative diseases, such as cancers, in mammals. The invention also relates to processes for the production of enantiomerically pure or optically enriched (+)- or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one enantiomers from a mixture containing two enantiomers using continuous chromatography. The invention further relates to the L-(+)-tartaric acid or (S)-(−)-1,1'-binapthyl-2,2'-diyl hydrogenphosphate salts of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one.

35 Claims, No Drawings

ENANTIOMERS OF 6-[(4-CHLORO-PHENYL)-HYDROXY-(3-METHYL-3H-IMIDAZOL-4-YL)-METHYL]-4-[3-(3-HYDROXY-3-METHYL-BUT-1-YNYL)-PHENYL]-1-METHYL-1H-QUINOLIN-2-ONE AND SALTS THEREOF, USEFUL IN THE TREATMENT OF CANCER

CROSS-REFERENCE TO RELATED APPLICATION

This is a divisional patent application of U.S. patent application Ser. No. 10/228,657 filed Aug. 27, 2002 now U.S. Pat. No. 6,740,757, which claims the benefit of U.S. Provisional Patent Application 60/315,740, filed Aug. 29, 2001, all of the aforementioned applications are hereby incorporated by reference in their entirety.

BACKGROUND OF THE INVENTION

This invention relates to the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, prodrugs thereof and pharmaceutically acceptable salts and solvates of said enantiomers and prodrugs. The compounds of the present invention are useful in the treatment of hyperproliferative diseases, such as cancers, in mammals. The compounds are also useful as inhibitors of the enzyme farnesyl protein transferase, which is involved in cancerous tumor growth.

In describing an optically active compound, the prefixes D and L or R and S are used to denote the absolute configuration of the molecule about its chiral center(s). The prefixes (+) and (−) or d or l are employed to designate the sign of rotation of plane-polarized light by the compound, with (−) or l meaning that the compound is levorotatory and with (+) or d meaning that the compound is dextrorotatory. For a given chemical structure the optically active isomers having opposite sign of optical rotation are called enantiomers. Said enantiomers are identical except that they are mirror images of each other. A 1:1 mixture of such enantiomer is called a racemic mixture.

It should be noted that optical rotation of chemical substances is dependent upon experimental parameters. The values shown hereinunder are specific rotations and the experimental conditions such as temperature, the wavelength of the plane polarized light used, the solvent as well as the concentration of the sample are indicated in the conventional way. The optical rotation may vary when for instance an acid addition salt is formed.

Stereochemical purity is of importance for biologically active substances that are used in pharmaceutical compositions for human application since the respective enantiomers may have a different potency or may have a different activity. Often, one of the enantiomers presents the desired optimum biological activity. Additionally, the presence of the other enantiomer in a composition or agent may cause or invigorate certain side effects. It is generally desirable to administer the biologically active substance in the form of a substantially pure enantiomer, which specifically exhibits the desired biological activity. Therefore, the resolution of a racemate into its enantiomers is often an important step in the preparation process of pharmacologically active substances.

The present invention provides for the enantiomers (−)- and (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, and derivatives thereof. The invention further provides a number of processes to isolate the enantiomers (−)- and (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, and the derivatives thereof, in high yields and in a high enantiomeric excess (e.e.). More particularly, the invention relates to the process for production of enantiomerically pure and/or optically enriched (−)- and (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one from a racemate mixture using continuous chromatography or chiral salt precipitation methods.

SUMMARY OF THE INVENTION

The invention relates to (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, prodrugs thereof and pharmaceutically acceptable salts and solvates of said compounds and prodrugs.

The present invention further relates to (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, L-(+)-tartaric acid and (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (S)-(−)-1,1'-binapthyl-2,2'-diyl hydrogenphosphate.

This invention also relates to a method for the treatment of abnormal cell growth in a mammal, including a human, comprising administering to said mammal an amount of one of the compounds described herein, prodrugs thereof, and pharmaceutically acceptable salts and solvates of said compounds and prodrugs, that is effective in treating abnormal cell growth or inhibiting farnesyl protein transferase.

In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal a therapeutically effective amount of one of the compounds described herein, prodrugs thereof, and pharmaceutically acceptable salts and solvates of said compounds and prodrugs in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The present invention also relates to a method for the treatment of an infection in a mammal, including a human, that is facilitated by farnesyl protein transferase, such as hepatitis delta virus or malaria, which comprises administering to said mammal a therapeutically effective amount of one of the compounds described herein, prodrugs thereof, and pharmaceutically acceptable salts and solvates of said compounds and prodrugs.

This invention also relates to a pharmaceutical composition for the treatment of abnormal cell growth in a mammal, including a human, comprising an amount of one of the compounds described herein, prodrugs thereof, and pharmaceutically acceptable salts and solvates of said compounds and prodrugs, that is effective in inhibiting farnesyl protein transferase, and a pharmaceutically acceptable carrier.

This invention also relates to a pharmaceutical composition for the treatment of abnormal cell growth in a mammal, including a human, comprising an amount of one of the compounds described herein, prodrugs thereof, and pharmaceutically acceptable salts and solvates of said compounds and prodrugs, that is effective in treating abnormal cell growth, and a pharmaceutically acceptable carrier.

The invention also relates to a pharmaceutical composition for the treatment of abnormal cell growth in a mammal, including a human, which comprises a therapeutically effective amount of one of the compounds described herein, prodrugs thereof, and pharmaceutically acceptable salts and solvates of said compounds and prodrugs, in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for the treatment of an infection in a mammal, including a human, that is facilitated by farnesyl protein transferase, such as malaria or hepatitis delta virus, comprising an amount of effective amount of one of the compounds described herein, prodrugs thereof, and pharmaceutically acceptable salts and solvates of said compounds and prodrugs, that is effective in treating abnormal cell growth, and a pharmaceutically acceptable carrier.

This invention also relates to processes for resolving the racemate 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one into its two enantiomers, (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, using either batch or continuous chromatography or salt crystallization.

The present invention also relates to a process for chromatographically resolving an enantiomerically pure or optically enriched (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one from a racemic mixture using continuous chromatography or single column high performance chromatography.

Some examples of continuous chromatography are liquid chromatography technologies known by the names cyclojet, and simulated moving bed chromatography (SMB). The concept of SMB was described in the late 1950's (U.S. Pat. Nos. 2,957,927 and 2,985,589) and has long been used in the petrochemical and sugar industries, Nicoud, R. M., LC-GC Intl, 5 (5), 43 (1992). Further reference can be made to U.S. Pat. Nos. 3,205,166; 3,291,726; and 3,310,486. A high efficiency continuous separation process using SMB is disclosed in U.S. Pat. Nos. 4,402,832; 5,518,625; 5,434,298; 5,434,299; 5,498,752; and Re 35,919, which are all incorporated by reference. In addition, "Chiral Discrimination on Polysaccharide Derivatives", Yashima and Okamoto, Bull. Chem. Soc. Jpn., 68, 3289–3307(1995) discusses separation characteristics useful in chiral chromatography phases. Further discussion by Okamoto et. al. are included in The Journal of Chromatography, Part A, Volume 694, pp 101–109 (1995).

SMB combines the high-resolution power of high performance liquid chromatography (HPLC) with the lower costs of classical separation processes such as crystallization. The costs of the SMB process can be reduced even further, if it is combined with a racemization step converting the undesired enantiomer into the racemic form, which could then be recycled back into the process to isolate more of the desired enantiomer. This results in a very efficient and productive method to isolate a desired enantiomer from a racemic mixture.

Other methods may also be employed to separate enantiomers such as the classic technique of chiral acid precipitation, which is described in applications EP 828,702 and WO 00/32554 and U.S. Pat. No. 4,571,424. The aforementioned applications and U.S. patent are hereby incorporated in their entirety by reference. Separation of enantiomers using chiral acids has been found by those of ordinary skill in the art to be a matter of trial and error. It is common even for experienced investigators to find that despite using a multitude of combinations of resolving agents and reaction conditions that chiral acid preparation is unsuccessful. The present invention provides a chiral acid precipitation of the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one in high enantiomeric excess and high optical purity.

The methods of the present invention are a substantial improvement over the method described in the '377 patent for preparing optically enriched 6-[(4-chloro-phenyl)-hydroxy-(3-methyl-3H-imidazol-4-yl)-methyl]-4-(3-ethynyl-phenyl)-1-methyl-1H-quinolin-2-one. The method described in Example 2 of the '377 patent employed high-performance liquid chromatography over CHIRALPAK™ AD. Both enantiomers were obtained with greater than 97% optical purity. The methods of the present invention involve an significant improvement of the method described in the '377 patent by providing stereoselective preparations which provide the desired enantiomers at very high purity levels in a cost effective manner. The methods of the present invention are particularly attractive for use in the commercial production of enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and the conversion of said enantiomers to either (−)- or (+)-6-[(4-chloro-phenyl)-hydroxy-(3-methyl-3H-imidazol- 4-yl)-methyl]-4-(3-ethynyl-phenyl)-1-methyl-1H-quinolin-2-one. Conversion of the isolated enantiomer to a desired salt form can be readily achieved.

The continuous chromatography comprises a liquid mobile phase comprising at least one polar solvent and a solid chiral stationary phase comprising a derivatized polysaccharide that is selected from the amylosic or cellulosic class of polysaccharides.

Some examples of the continuous chromatography methods are simulated moving bed chromatography process or the cyclojet process. The simulated moving bed chromatography process is preferred. The process uses a chiral stationary phase which is a member of the amylosic or cellulosic class of polysaccharides selected from amylose 3,4-substituted phenyl carbamate, cellulose 3,5-disubstituted phenyl carbamate or cellulose 4-substituted benzoate. Preferably the chiral stationary phase is an analog of amylose tris (3,5-substituted phenyl carbamate) wherein the substituent is 3,5-dimethyl. The chiral stationary phase can also preferably be a cellulose 3,5-disubstituted phenyl carbamate or cellulose 4-substituted benzoate polysaccharide analog. Preferably the chiral stationary phase is cellulose tris (3,5-dimethylphenyl) carbamate or cellulose tris (4-methylbenzoate).

The mobile phase comprises a solvent that is selected from heptane, hexane, isopropyl, ethanol, methanol, methyl acetate, acetonitrile, methylene chloride, ethyl acetate and/or mixtures thereof. Preferably the mobile phase is selected from mixture of heptane and ethanol or isopropanol and/or a mixture of methanol and ethanol with or without heptane. In one embodiment the chiral stationary phase is amylose tris(3,5-dimethylphenylcarbamate) with a mobile phase 50:50 of heptane and ethanol. In one preferred embodiment the chiral stationary phase is amylose tris(3,5-dimethylphenylcarbamate) and the mobile phase is 50:50 mixture of methanol and ethanol. The chromatographic retention times are increased or decreased by varying the mobile phase components. The separation affords at least one of the enantiomers recovered is greater than or equal to 90 percent. The temperature range is about 5 to 45° C., preferably 20 to 40° C., more preferably 25° C. The separation factor alpha "α" is about 1.1 to 4.0. Using a temperature of about 25° C. takes advantage of an increased solubility of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one in the mobile phase. The chiral stationary phase polysaccharide derivative can also be immobilized on silica gel, zirconium, alumina, ceramics and other silicas.

The invention also relates to the salt separation of the enantiomers 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one using L-(+)-tartaric acid or (S)-(−)-1,1'-binapthyl-2,2'-diyl hydrogenphosphate salts.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "pharmaceutically acceptable salt(s)", as used herein, unless otherwise indicated, includes salts of acidic or basic groups that may be present in the compounds of present invention. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

The term "prodrug", as used herein, unless otherwise indicated, means compounds that are drug precursors, which following administration, release the drug in vivo via some chemical or physiological process (e.g., a prodrug on being brought to the physiological pH is converted to the desired drug form).

The free hydroxy group of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one can be converted into a prodrug. Prodrugs include compounds wherein an amino acid residue, or a polypeptide chain of two or more (e.g., two, three or four) amino acid residues is covalently joined through the hydroxy group of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, the free hydroxy group may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

The subject invention also includes isotopically-labelled compounds, and the pharmaceutically acceptable salts thereof, which are identical to (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but- 1-ynyl)-phenyl]-1-methyl-1H-quinolin-2-one, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, and prodrugs thereof can generally be prepared by carrying out the procedures disclosed in the Schemes and/or in the Examples and Preparations of the '377 patent by substituting a readily available isotopically labelled reagent for a nonisotopically labelled reagent.

It will be appreciated that any solvate (e.g. hydrate) form of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one or (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and prodrugs thereof can be used for the purpose of the present invention.

DETAILED DESCRIPTION OF THE INVENTION

The present invention provides for the enantiomers (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, prodrugs thereof and pharmaceutically acceptable salts and solvates of said enantiomers and prodrugs that are useful in the treatment of hyperproliferative diseases, such as cancers, in mammals.

The invention also relates to the L-(+)-tartaric acid or (S)-(−)-1,1'-binapthyl-2,2'-diyl hydrogenphosphate salts of the (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one.

The preparation of the racemate 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one may be prepared in the manner described in Example 4 of U.S. Pat. No. 6,150,377 ("the '377 patent") by replacing 3-methyl-1-butyne with 3-hydroxy-3-methyl-1-butyne. The '388 patent is hereby incorporated by reference in its entirety. The racemate 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one is useful in the preparation of the cancer treating compound 6-[(4-chloro-phenyl)-hydroxy-(3-methyl-3H-imidazol-4-yl)-methyl]-4-(3-ethynyl-phenyl)-1-methyl-1H-quinolin-2-one which is also described in U.S. Pat. No. 6,150,377 ("the '377 patent"), which is hereby incorporated by reference in its entirety. The racemate, 6-[(4-chloro-phenyl)-hydroxy-(3-methyl-3H-imidazol-4-yl)-methyl]-4-(3-ethynyl-phenyl)-1-methyl-1H-quinolin-2-one, its enantiomers and pharmaceutically acceptable salts are also useful as inhibitors of the enzyme farnesyl protein transferase.

The '377 patent also describes the separation of the enantiomers of the racemate 6-[(4-chloro-phenyl)-hydroxy-(3-methyl-3H-imidazol-4-yl)-methyl]-4-(3-ethynyl-phenyl)-1-methyl-1H-quinolin-2-one using high performance liquid chromatography (HPLC). However, the '377 patent does not specifically describe the separation of the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one. 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one has one chiral center and thus exists in two enantiomeric forms, i.e., (+) or (−).

The racemate, 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, may be separated into its two enantiomers using chromatography techniques, such as high performance liquid chromatography (HPLC) or simulated moving bed chromatography (SMB). The separated enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one may be converted if desired into the corresponding enantiomers of 6-[(4-chloro-phenyl)-hydroxy-(3-methyl-3H-imidazol-4-yl)-methyl]-4-(3-ethynyl-phenyl)-1-methyl-1H-quinolin-2-one. Salt forms of the free bases 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and 6-[(4-chloro-phenyl)-hydroxy-(3-methyl-3H-imidazol-4-yl)-methyl]-4-(3-ethynyl-phenyl)-1-methyl-1H-quinolin-2-one are readily prepared and are useful in the treatment of hyperproliferative diseases, such as cancers, in mammals, especially humans.

If the preparation of an optically enriched enantiomer of 6-[(4-chloro-phenyl)-hydroxy-(3-methyl-3H-imidazol-4-yl)-methyl]-4-(3-ethynyl-phenyl)-1-methyl-1H-quinolin-2-one is desired the methods of the present invention offer significant advantages over the method disclosed in the '377 patent. Once the desired enantiomer has been isolated it can be readily converted into a desired salt. It is advantageous to resolve a racemate into its enantiomers at the earliest stage of the synthesis in order to minimize the amount of superfluous ballast carried through the reaction sequence. The '377 patent describes the separation of the enantiomers of 6-[(4-chloro-phenyl)-hydroxy-(3-methyl-3H-imidazol-4-yl)-methyl]-4-(3-ethynyl-phenyl)-1-methyl-1H-quinolin-2-one followed by conversion to the desired salt. The penultimate racemate formed in the synthesis of [(4-chloro-phenyl)-hydroxy-(3-methyl-3H-imidazol-4-yl)-methyl]-4-(3-ethynyl-phenyl)-1-methyl-1H-quinolin-2-one is 6-[(4-chloro-phenyl)-hydroxy-(3-methyl-3H-imidazol-4-yl)-methyl]-4-[3-(3-hydroxy-3-methyl-but-1-ynyl)-phenyl]-1- methyl-1H-quinolin-2-one. No resolution of the penultimate racemate or its derivatives thereof have been described previously.

It has been found that racemate resolution of 6-[(4-chloro-phenyl)-hydroxy-(3-methyl-3H-imidazol-4-yl)- methyl]-4-[3-(3-hydroxy-3-methyl-but-1-ynyl)-phenyl]-1-methyl-1H-quinolin-2-one can be carried out by salt resolution and chromatographic methods. Each of the methods provide significant advantages over the previously disclosed separation of the racemate 6-[(4-chloro-phenyl)-hydroxy-(3-methyl-3H-imidazol-4-yl)-methyl]-4-(3-ethynyl-phenyl)-1-methyl-1H-quinolin-2-one in the '377 patent.

More particularly it has been found that using chromatographic methods described below results in a surprising enhancement in productivity thus providing more enantiomer per kg of chiral stationary phase. This has significant economic benefits over the disclosed resolution of enantiomers in the '377 patent. This provides a commercial attractive method in which to prepare the enantiomers 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one. The enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one can be readily converted to the enantiomers of 6-[(4-chloro-phenyl)-hydroxy-(3-methyl-3H-imidazol-4-yl)-methyl]-4-(3-ethynyl-phenyl)-1-methyl-1H-quinolin-2-one. Additionally, racemization of the undesired 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one enantiomer is more facile than that of corresponding undesired 6-[(4-chloro-phenyl)-hydroxy-(3-methyl-3H-imidazol-4-yl)-methyl]-4-(3-ethynyl-phenyl)-1-methyl-1H-quinolin-2-one enantiomer due to the protection of the alkynyl hydrogen.

Furthermore, single enantiomers are more soluble than their racemic forms and thus downstream reactions can be more concentrated and have higher volumetric productivity (further improved by the fact that only the desired isomer is being carried forward). This significantly improves the economics of the resolution.

Chromatography comprises a liquid mobile phase comprising at least one polar solvent and a solid chiral stationary phase (CSP) comprising a derivatized polysaccharide that is selected from the amylosic or cellulosic class of polysaccharides. The amylosic or cellulosic class of polysaccharides are selected from cellulose tribenzoate, cellulose tricarbamate, and amylose tricarbamate. Preferably the chiral stationary phase is an analog of amylose (3,5-substituent phenyl carbamate) wherein the substituent is 3-methyl, 5-methyl.

The mobile phase comprises a solvent that is selected from heptane, hexane, isopropanol, ethanol, methanol, methyl acetate, acetonitrile, methylene chloride, ethyl acetate and/or mixtures thereof. Preferably the mobile phase is selected from ethanol, isopropanol, methanol or heptane and/or binary or ternary mixtures of the solvents. A list of acceptable combinations of mobile phases and solvents is given in Table I below. In one embodiment the chiral stationary phase is amylose tris(3,5-dimethylphenyl carbamate) with a mobile phase of ethanol/methanol wherein the percentage of ethanol in the mobile phase mixture is greater than 30%. Preferably the chiral stationary phase is amylose tris (3,5-dimethylphenyl carbamate) and the mobile phase is ethanol/heptane wherein the percentage of ethanol in the mobile phase mixture is greater than 30%. The chromatographic retention times are increased or decreased by varying the mobile phase components. The separation affords recovery of greater than or equal to 90 percent of at least one of the enantiomers. The temperature range is about 5 to 45° C., preferably about 20 to 40° C., and more preferably about 22 to 30° C. The separation factor a is about 1.2 to 5.0, preferably about 1.5 to 4, and more preferably about 2 to 4.

Using a temperature of about 25° C. takes advantage of an increased solubility of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one in the mobile phase. The chiral stationary phase polysaccharide derivative can be immobilized on silica gel, zirconium, alumina, ceramics and other silicas.

Examples of suitable CSP and mobile phases for the 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one are shown in the Table 1 below.

TABLE 1

| CHIRAL STATIONARY PHASE SELECTOR | MOBILE PHASE MIXTURE | TEMP ° C. | UV (nm) | α |
|---|---|---|---|---|
| Amylose tris (3,5-dimethylphenyl carbamate) | Heptane/ethanol<br>Methanol/ethanol<br>Methanol/ethanol/heptane<br>Heptane and isopropanol | 25 | 230 | 1.1–4.0 |
| Cellulose tris (3,5-dimethylphenyl carbamate) | Heptane/ethanol<br>Heptane/isopropanol | 25 | 230 | ~1.3 |
| Cellulose tris (4-methylbenzoate) | Heptane/ethanol | 25 | 230 | 1.1 |

The UV Wavelength represents the detector wavelength used to monitor the elution of the two enantiomers. Alpha "α" represents the separation factor for the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one separation using a single column which is 4.6 mm ID×250 mm.

Batch chromatographic purification is achieved using a system comprising a high pressure positive displacement pumping system, a sample injection mechanism (either injection loop or pump), a packed column containing the CSP, a UV detector and a mechanism to collect fractions. The column is equilibrated in the desired mobile phase and then the sample is injected onto the column. The column effluent is then monitored at a UV wavelength where the product absorbs. As the first enantiomer (less retained enantiomer) elutes a fraction containing predominately the first enantiomer is collected. As the UV absorbance of the first enantiomer peak decreases, the effluent is then switched to a second collection vessel, The second collection vessel collects the portion of the enantiomers that elude at around the same point, which occurs if separation factor is close to 1. As the absorbance due to the second enantiomer (more retained enantiomer) elute, the effluent is then switched to a third vessel to collect pure second enantiomer. When the absorbance of the second enantiomer decreases to a low level, the fraction collection is stopped. Multiple cycles of injection and collection are repeated until the desired amount of enantiomers is collected.

Continuous chromatography can be utilized in the present invention to separate the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one. One example of continuous chromatography is the cycloject method, which is described in U.S. Pat. No. 5,630,943, incorporated herein by reference. Another continuous chromatographic method that may be employed to separate the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one is Simulated Moving Bed Chromatography (SMB) as described in U.S. Pat. Nos. 5,470,464; 5,705,061; 5,422,077; 5,456,825 and EPO 586,385, each of the aforementioned U.S. patents and European application is incorporated herein by reference.

SMB chromatography for the production of enantiomerically pure and/or optically enriched 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one from a mixture containing two enantiomers is described below. The purification is achieved using SMB comprising a set of columns packed with a chromatographic CSP capable of chiral recognition; ports for the continuous introduction of solvent desorbent (mobile phase) and feed; ports for the continuous removal of raffinate (solution containing the less strongly retained enantiomer) and extract (solution containing the more strongly retained enantiomer); and a means of recycling fluid through the system, if necessary. The columns are connected such that the outlet of each column is connected to the inlet of the next column also with the outlet of the last column being connected to the inlet of the first column.

The following general procedures for continuous chromatography in Examples of the present invention were followed. Using the experimental conditions described herein it was found that the (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one enantiomer was more retained and was recovered in the extract stream.

The optimization of the operating conditions of a SMB is preferably done using a simulation tool, a methodology based on the modeling/simulation of non-linear chromatography as described in Charton F., and Nicoud, R. M., J. Chrom., 702, 97–112 (1995).

In order to enhance productivity and yield of the enantiomer separated using SMB racemization may be employed. Under the SMB conditions employed for the separation of the enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one the (−) enantiomer was less retained. If the desired enantiomer is the (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one then the less retained (−) enantiomer may be racemized using any of the methods described in Example 4. Racemization of the less retained enantiomer results in a more productive method to isolate the desired more retained enantiomer. Using racemization there are two options to run the SMB separation process to enhance productivity, yield and optical purity. In the first option the more retained enantiomer is mostly recovered in the extract and the solution to be racemized contains almost exclusively the less retained enantiomer. In the second option the more retained enantiomer is partly recovered in the extract and the solution to be racemized contains a significant amount of both enantiomers.

When the first option is chosen the amount of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one to be racemized is minimized, but when the second option is chosen it is possible to increase the SMB throughput and enhance the daily productivity of the process.

The two options were studied first by numerical simulations, which allow one to make a fast parametric study of the process. In the case of the second option the recovery yield of the less retained enantiomer in the raffinate was an additional parameter that could be varied to achieve optimum performance. It was found that a recovery yield of above 90% leads to a good compromise between the improvement of the SMB performance and the increase of the amount of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one to be racemized.

In the case of large-scale enantiomeric separations by SMB the cost of the purification is mainly linked to the productivity, the influence of the eluent consumption being secondary. Consequently, in the present case where racemization is expected to be relatively inexpensive, the second option has a clear advantage in increasing the SMB throughput and consequently an enhanced productivity.

A schematic depicting the SMB purification and racemization step is shown below:

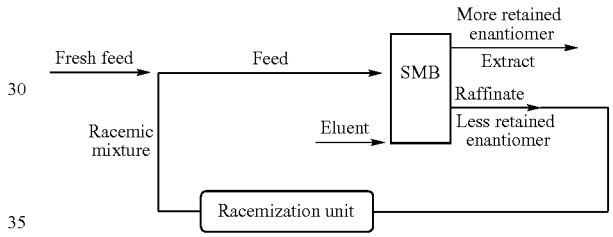

The more retained enantiomer (+) may be recovered at the required optical purity (95–99.9%) in the extract stream whereas the less retained enantiomer (−) may be collected in the raffinate stream. It may be possible to recycle the stream enriched in the undesired enantiomer through a racemization unit, which would decrease the necessary amount of new racemic feed required.

Two examples of the SMB optimization follow which are optimized near the 90–95% recovery of the (+) enantiomer considered to be optimum as described above.

Other enantiomeric separation techniques may also be employed to separate the enantiomers of the racemate, 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one. One preferred method of separating the enantiomers of the racemate 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one is salt crystalization techniques.

The Dutch method of salt resolution screening (Broxterman et al., Dutch Resolution, A New Technology in Classical Resolution, Chim. Oggi. 16(9), 34–37, (1998)) may be used to determine the optimal chiral acid for the resolution. In this method several chiral acids from a family (i.e., tartaric acid derivatives) were added to the free base 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one to be resolved. The organic solvent screened in the process may be any such solvent in which the salt formed from the 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one to be resolved and a chiral acid is soluble at elevated temperature but insoluble at ambient temperatures. Exemplary of suitable solvents are methanol, ethanol, 2-propanol, n-butanol, acetone, methyl ethyl ketone, ethyl acetate, t-butyl acetate, methylene chloride and mixtures thereof.

In a typical procedure a mixture of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one and mixture of a family of acids were dissolved in a solvent by the application of heat. Upon cooling to room temperature any crystals that formed were isolated. Analysis was performed using HPLC on the free base of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one which was obtained by treatment of approximately 10 mg the salt of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one with 0.5M NaOH and EtOAc (1 mL of both). The following are the conditions under which the HPLC were performed: CHIRALPAK™ AD resin (manufactured by Daicel Chemical Industries, Ltd., Osaka, Japan); solvent system 30% isopropanol/70% heptane, UV 210 nm or 340 nm. The (−)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one eluded after 5.6 minutes while the (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one eluded after 13.6 minutes. The HPLC method described above to determine the presence of the desired enantiomer was also performed for Examples of the present application. The e.r can be readily assertained by dividing the area of the enantiomer of interest by the total area of the two enantiomers.

The racemates, enantiomers, prodrugs, solvates and their pharmaceutically acceptable salts (herein referred to as "the active compounds") exhibit activity as Ras farnesylation inhibitors and are useful in the treatment of cancer and the inhibition of abnormal cell growth in mammals, including humans. The abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

In another embodiment the abnormal cell growth is a benign proliferative disease, including, but not limited to, psoriasis, benign prostatic hypertrophy or restinosis. The racemates, enantiomers and their pharmaceutically acceptable salts are useful in inhibiting farnesyl protein transferase.

The enantiomers of the present invention are basic in nature and are capable of forming a wide variety of different salts with various inorganic and organic acids. Although such salts must be pharmaceutically acceptable for administration to animals, it is often desirable in practice to initially isolate the active compound from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the active compounds are similarly prepared except through reaction of a carboxy group with an appropriate cationic salt reagent, such as sodium, potassium, calcium, magnesium, ammonium, N,N'-dibenzylethylenediamine, N-methylglucamine (meglumine), ethanolamine, tromethamine, or diethanolamine.

The active compounds of the present invention can be administered orally, transdermally (e.g., through the use of a patch), parenterally, topically or rectally. Oral administration is preferred. In general, compounds are most desirably administered in dosages ranging from about 1.0 mg up to about 500 mg per day, preferably from about 1 to about 100 mg per day in single or divided (i.e., multiple) doses. The active compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of active compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the active compounds topically and this may preferably be done by way of creams, jellies, gels, pastes, ointments and the like, in accordance with standard pharmaceutical practice.

The active compounds may also be administered to a mammal other than a human. The dosage to be administered to a mammal will depend on the animal species and the disease or disorder being treated. The active compounds may be administered to animals in the form of a capsule, bolus, tablet or liquid drench. The active compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The activity of the active compounds as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approximately 40 grams fresh tissue in 100 ml of sucrose/MgCl$_2$/EDTA buffer (using a Dounce homogenizer; 10–15 strokes), centrifuging the homogenates at 1000×g for 10 minutes at 4° C., re-centrifuging the supernatant at 17,000×g for 15 minutes at 4° C., and then collecting the resulting supernatant. This supernatant is diluted to contain a final concentration of 50 mM Tris HCl (pH 7.5), 5 mM DTT, 0.2 M KCl, 20 µM ZnCl$_2$, 1 mM PMSF and re-centrifuged at 178,000×g for 90 minutes at 4° C. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase ($^3$H) Scintillation Proximity Assay (SPA) kit (TRKQ 7010). FTase enzyme activity is determined in a volume of 100 µL containing 50 mM N-(2-hydroxy ethyl) piperazine-N'-(2-ethane sulfonic acid) (HEPES), pH 7.5, 30 mM MgCl$_2$, 20 mM KCl, 25 mM Na$_2$HPO$_4$, 5 mM dithiothreitol (DTT), 0.01% Triton X-100, 5% dimethyl sulfoxide (DMSO), 20 µg of crude FTase, 0.12 µM [$^3$H]-farnesyl pyrophosphate ([$^3$H]-FPP; 36000 dpm/pmole, Amersham LifeScience), and 0.2 µM of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 µL of steptavidin-coated SPA beads (RPNQ0007) per well and incubating the reaction mixture for 30 minutes at room temperature. The amount of radioactivity bound to the SPA beads is determined using a MicroBeta 1450 plate counter. Under these assay conditions, the enzyme activity is linear with respect to the concentrations of the prenyl group acceptor, Bt-KTKCVIS, and crude FTase, and inhibition of Bt-KTKCVIS interaction with FTase can be detected. The enzyme activity is saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound versus its incorporation in control wells (absence of inhibitor). An IC$_{50}$ value, that is, the concentration required to produce half maximal farnesylation of Bt-KTKCVIS, is determined for each compound from the dose-responses obtained.

The present invention is illustrated by the following Examples. It will be understood, however, that the invention is not limited by the specific details of the following Examples.

EXAMPLE 1

Preparation of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one A clean, dry, 500 gallon glass lined reactor was charged with 50 Kg of (4-(3-Bromo-phenyl)-6-(4-chloro-benzoyl)-1-methyl-1H-quinolin-2-one) (110 moles, 1 eq) followed by 4.65 Kg of Bis(triphenylphosphine)palladium (II) chloride (6.63 moles, 0.06 eq) and 1.26 Kg Copper (I) Iodide (6.63 moles, 0.06 eq). Then charged 55 gallons of TEA (1492 moles, 13.6 eq) and 110 gallons of THF (8.33V), this was followed by the addition of 13.9 Kg of 2-methyl-3-butyn-2-ol (165 moles, 1.5 eq). The stirred mixture was then heated to 60–65° C. for 18 hours, the reaction tank was attached to a scrubber tank containing aqueous sulfuric acid to reduce TEA odor, a slight positive N2 stream is maintained to assure vapors migrate to the scrubber.

The reaction was cooled to 18–23° C. and sampled for HPLC analysis and the reaction was deemed complete. Then charged to the reaction 16.5 Kg of Darco G-60 and 16.5 Kg of Filter aid (celite), the resulting mixture was stirred for 2 hours. The entire reaction mixture was then filtered through a celite coated filter and the filter cake washed with 55 gallons of THF (4.16V). The filtrate was charged to a 300 gallon glass lined reactor and vacuum concentrated to a volume of ~130–135 gallons while maintaining a pot temperature of less than 65° C. The concentrate was then displaced with 330 gallons of 1,2-Dichloroethane (25V) while still maintaining a pot temperature less than 65° C. At the end of the displacement a further 55 gallons of 1,2-dichloroethane (4.2V) was added.

Then charged to the reactor an aqueous ammonium chloride solution that was pre-prepared by dissolving 50 Kg of ammonium chloride in 106 gallons of water. The resulting mixture was stirred for 2 hours and then the layers were allowed to settle. The lower organic layer was removed and the upper ammonium chloride aqueous drummed up. The organic layer was returned to the tank and charged an aqueous Sodium bicarbonate wash that was pre-prepared by dissolving 20 Kg of sodium bicarbonate in 106 gallons of water. The resulting mixture was stirred for 2 hours and then the layers were allowed to settle. The lower organic layer was separated and the aqueous layer drummed up. The organic layer was returned to the tank and the above aqueous sodium bicarbonate wash repeated.

After the layers are separated and the organic layer returned to the tank, 106 gallons of fresh water was charged and the mixture stirred for 2 hours. The layers were settled and separated and the organic layer charged back to the tank. The charged a pre-prepared solution of 50 Kg Sodium chloride dissolved in 106 gallons of water and stirred for 2 hours. The layers were settled and separated and the organic layer charged to a clean, dry, 300 gallon glass lined reactor.

The DCE solution was then vacuum concentrated to 60–70 gallons, this concentrate was then vacuum displaced with 165 gallons of Toluene while maintaining a pot volume of 60–70 gallons and a temperature less than 65° C. The resulting slurry was cooled to 18–23° C. and granulated for 6 hours.

The slurry was filtered and the solid filter cake washed with 15 gallons of Toluene followed by 15 gallons of Hexane. The solids were vacuum dried at 40–45° C. for 15 hours, this resulted in 43.7 Kg of 6-(4-Chloro-benzoyl)-4-[3-(3-hydroxy-3-methyl-but-1-ynyl)-phenyl]-1-methyl-1H-quinolin-2-one) (86.7% yield).

To a clean, dry, glass lined reactor was charged 87 Kg of (5-bromo-1-methylimidazole mesylate salt, 338 moles, 1eq) and 86 gallons of MTBE (methyl tert-butyl ether) (3.75V). Then charged 16 gallons of water (0.716V) and the stirred mixture was cooled to 10–15° C. Then added slowly to the cooled mixture 21 liters of 50% sodium hydroxide (1.2 eq) keeping the internal temperature below 24° C. When this addition was complete the mixture was stirred at ambient temperature for 30 minutes. At this point the pH of the aqueous layer was seen to be 13.0. The layers were allowed to settle and the lower aqueous layer separated. The organic layer was drummed and the aqueous layer returned to the tank along with 43 gallons of MTBE (1.87V) and the mixture stirred for 30 minutes. The layers were allowed to settle and the lower aqueous layer separated. The first drummed organic layer was returned to the tank and combined with the MTBE backwash. To the organic layer was charged 9 gallons of water and the mixture stirred for 30 minutes. The layers were allowed to settle and separated away the lower aqueous layer. Then charged 8 gallons of saturated sodium chloride solution and stirred for 30 minutes. The layers were allowed to settle and the lower aqueous separated. The organic layer was charged to a clean, dry, 500 gallon glass lined tank and added 27 Kg of anhydrous magnesium sulfate and stirred the resulting mixture for 3 hours. The spent drying agent was filtered off and the filter cake washed with 10 gallons of MTBE. The organic filtrate was charged back to the tank and added 40 Kg of 4A molecular sieves and the mixture slowly stirred for 20 hours. The mixture was filtered and the filtrate sent to a clean, dry, and nitrogen purged 500 gallon glass lined tank, the filter cake was washed with 10 gallons of MTBE.

To a clean, dry, and nitrogen purged 500 gallon glass lined reactor charged 200.4 Kg of the 5-bromo-2-methylimidazole free base solution in MTBE (as described above). This contained 22.3 Kg (138 moles, 4 eq) of the imidazole free base. This solution was vacuum stripped to an oil maintaining an internal temperature of 20–250C. The charge to the concentrated oil, 6 gallons of THF (1.42 V) and 165 gallons of methylene chloride (40 V) and the resulting mixture stirred to obtain a solution.

Then slowly charged to the reaction mixture over 55 minutes, 116 Kg (37 gallons) of 1.0 Molar ethyl magnesium bromide in MTBE (138 moles, 4 eq), while keeping the internal temp below 24° C. The reaction was then stirred at 15–24° C. for 8 hours. The reaction was sampled for HPLC analysis and the grignard formation was deemed complete.

Then charged slowly to the grignard reaction mixture, 15.8 Kg of CP-729,134 (34.6 moles, 1 eq) dissolved in 59 gallons of methylene chloride (14 V) keeping the internal temperature below 250C. The addition of this solution took 30 minutes. The charge tank was rinsed with 21 gallons of methylene chloride (5 V) and this rinse charged to the reaction mixture. The entire reaction mixture was then heated to 4045° C. for 8 hours. After cooling to 20–25° C. the reaction was sampled for HPLC analysis and the reaction deemed complete.

Then charged to the reaction mixture over 30 minutes a solution of 80.2 Kg of ammonium chloride dissolved in 156 gallons of water. The biphasic mixture was stirred for 30 minutes, the layers allowed to settle and separated. The organic layer was returned to the tank and 156 gallons of fresh water charged. The layers were stirred for 30 minutes, allowed to settle, and the layers separated. The organic layer was charged to a clean, dry, 500 gallon glass lined reactor and then heated to atmospherically distilled of methylene chloride until a volume of 18–20 gallons was reached.

This resulted in a slurry, the temperature was allowed to cool to 15–20° C. and the slurry granulated for 2 hours. The solids were filtered off and the filter cake washed with 10 gallons of methylene chloride.

The isolated solids were vacuum dried at 40–45° C. for 16 hours, this gave 16.4 Kg of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one (88% yield). This material was 99.7% pure by HPLC area percent.

EXAMPLE 2

HPLC Batch Chromatography 240 grams of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one was dissolved in 9.45 liters of a 70/30/0.1 mix of heptane/isopropanol/diethylamine. Approximately 1.3 liters of this solution was then loaded onto a 15 cm×25 cm column packed with CHIRALPAK™ AD resin (manufactured by Daicel Chemical Industries, Ltd., Osaka, Japan). The column was eluted with the same solvent mix as the feed was dissolved in at a flow rate of 1000 ml/min. The effluent was monitored at 310 nm. Two distinct peaks were collected. The cycle of loading and eluting was repeated until all 9.45 liters were separated. A composite containing the cuts of the early eluting enantiomer (−)-6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one was made and concentrated to dryness to give 115 grams of solids which had and enantiomeric excess of 98%. A composite of the cuts from the second eluting enantiomer (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one was made and also concentrated to dryness to give 115 grams of solids which had an enantiomeric excess of 97%. The yield to both enantiomers was about 96% of theory. The productive yield of the process described above was about 0.5 kg of enantiomer produced per kg of chiral stationary phase per day.

In contrast using batch HPLC separation of 6-[(4-chloro-phenyl)-hydroxy-(3-methyl-3H-imidazol-4-yl)-methyl]-4-(3-ethynyl-phenyl)-1-methyl-1H-quinolin-2-one as described in the '377 patent gives a productivity of only 0.0093 kg of enantiomer per kg of chiral stationary phase per day. The process for separation of enantiomers of 6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one is over 500 times more productive than the process employed to separate racemic 6-[(4-chloro-phenyl)-hydroxy-(3-methyl-3H-imidazol-4-yl)-methyl]-4-(3-ethynyl-phenyl)-1-methyl-1H-quinolin-2-one. Use of the present process provides significant commercially advantages including lower cost, smaller columns, and employment of less resin for separation, which results in large savings in production costs.

EXAMPLE 3

Separation of Enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one Using SMB with Heptane/Ethanol Mobile Phase The racemate, 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one was separated using the SMB process described in the specification. The eluent employed was a 50:50 mixture of ethanol and heptane. The SMB operating parameters employed are shown in the following

TABLE 2

| Column: (CSP) | CHIRALPAK ™ AD |
|---|---|
| Mobile Phase: | 50% ethanol/50% heptane |
| Column Length: | 10.7 cm |
| Column I.D.: | 5.0 cm |
| Number of Columns: | 6 columns |
| Feed Concentration: | 12 gms/liter |
| Eluent Flow-rate: | 200 ml/min |
| Feed Flow Rate: | 81 ml/min |
| Flow Rate in Zone I: | 347 ml/min |
| Extract Flow Rate: | 179 ml/min. |
| Raffinate Flow Rate | 102 ml/min. |
| Period | 1.37 min |
| Temperature | 25° C. |
| Operating pressure | 55 bars |

The performance characteristics using SMB are shown in Table 3 below. The SMB process provides a productivity of 0.76 kg of enantiomer per day per kilogram of the chiral stationary phase employed.

TABLE 3

| SMB PERFORMANCE CHARACTERISTICS | |
|---|---|
| More retained enantiomer purity (%) | 99.5 |
| More retained enantiomer recovery yield (%) | 92.5 |
| Calculated volume of eluent necessary (l/g enantiomer) | 0.62 |
| Productivity (kg enantiomer/day/kg Chiral Stationary Phase) | 0.76 |
| Amount of feed to be processed (g/g enantiomer recovered) | 2.16 |
| Amount of product to be racemized (g/g enantiomer recovered) | 1.16 |

EXAMPLE 4

Separation of Enantiomers of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one Using SMB with Ethanol/Methanol Mobile Phase The racemate, 6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, was separated using the SMB process as described in the specification using a 50:50 mixture of heptane and ethanol as the eluent. The SMB operating parameters employed are shown in the following

TABLE 4

| SMB OPERATING PARAMETERS | |
|---|---|
| Type of Chiral Column: | CHIRALPAK ™ AD |
| Mobile Phase: | 50/50 v/v ethanol/methanol |
| # Columns | 6 |
| Column Length: | 10.7 cm |
| Column I.D.: | 5.0 cm |
| Feed Concentration (g/liter) | 20 |
| Feed Flow Rate: (ml/min) | 26 |
| Eluent Flow-rate (ml/min) | 197 |
| Flow Rate in Zone I | 415.3 ml/min |
| Extract Flow Rate: (ml/min) | 168.4 |
| Raffinate flow rate (ml/min) | 54.6 |
| Period | 0.79 |
| Temperature | 25° C. |
| Pressure (bar) | 40 |

The performance characteristics using SMB with the heptane/ethanol mixture are shown in Table 5 below. Compared to Example 3 this SMB process is not as productive, however, there is a decrease in the amount of eluent required per gram of the enantiomer. Accordingly, this process requires less solvent while still being a very productive way of preparing 6-[(4-chloro-phenyl)-hydroxy-(3-methyl-3H-imidazol-4-yl)-methyl]-4-(3-ethynyl-phenyl)-1-methyl-1H-quinolin-2-one.

TABLE 5

| SMB PERFORMANCE CHARACTERISTICS | |
|---|---|
| More retained enantiomer purity (%) | 99.4 |
| More retained enantiomer recovery yield (%) | 95 |
| Calculated volume of eluent necessary (liter/gm enantiomer) | 0.60 |
| Productivity (kg enantiomer per day per Kg CSP) | 0.63 |

TABLE 5-continued

| SMB PERFORMANCE CHARACTERISTICS | |
|---|---|
| Amount of feed to be processed (Kg per Kg enantiomer recovered) | 2.10 |
| Amount of product to be racemized (Kg per Kg enantiomer recovered) | 1.10 |

EXAMPLE 5

Racemization Processes For (−)-6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one (−)-6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one may be racemized using any of the following methods (A)–(C). However, Method A is preferred over Methods B or C, since it results in complete racemization.

Method A

The less retained enantiomer [(−)-6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one] was dissolved in 3 volumes of dimethyl formamide/water (5/1 mix). One volume of p-toluenesulfonic acid was added and complete racemization was seen after 4 hours.

Method B

The (−) enantiomer was dissolved in 10 volumes of a 5/1 mix of toluene and water. One volume of formic acid was added and the solution was refluxed for 14 hours. The analysis showed 40% of the (+) enantiomer.

Method C 10 volumes of a 10/1 mix of tetrahydrofuran and water were added to the (−) enantiomer and 1 volume of trifluoroacetic acid was added and the mixture was refluxed for 3 days. The solution was then analyzed and found to have 14% of the (+) enantiomer.

EXAMPLE 6

Salt Resolution of 6-[(4-Chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one Using L-(+)-Tartaric Acid 100 gms of racemic, 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one (0.186 moles) and 27.9 gms of (+)-2,3-dihydroxy butanedioate (0.186 moles, 1 eq ) was added to a 3-neck round bottom flask fitted with mechanical stirring, reflux condenser, thermocouple probe and a heating mantel. To the above reactants was added 2,300 mls of 2-propanol and 23 mls of water and the resulting white slurry heated. As the mixture was heated, solids were seen to dissolve, at reflux the solution was a slight haze. Heating was stopped and the mixture allowed to slowly cool. At 65° C. 20 mg of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (+)-2,3-dihydroxy butanedioate (e.r. 99:1) seed was added and cooling/crystallization continued. When the reaction mixture reached ambient temperature the resulting white slurry was granulated for 5 hours. The solids were isolated by vacuum filtration and the filter cake washed with 50 mls of dry 2-propanol, the solids were vacuum dried at 40–45° C. to give 53.1 gms (41.5% overall yield) of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (+)-2,3-dihydroxy butanedioate. Using chiral HPLC as described in the specification showed an e.r. of 96.3:3.6. NMR indicates ~3% 2-propanol present. Optical rotation of +32.9° in methanol using Na light source with a 1 decimeter cell (c=1.1013 gm/100 mls).

EXAMPLE 7

Repulp of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (+)-2,3-dihydroxy butanedioate to improve e.r.

2 gms of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (+)-2,3-dihydroxy butanedioate with a e.r. of 97.2:2.8 was slurried in 30 mls (15V) of dry 2-propanol for 4–5 hours. The solids are isolated by vacuum filtration and washed with a small amount of dry 2-propanol. After vacuum drying the solids overnight at 40–45° C. 1.8 gms of (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (+)-2,3-dihydroxy butanedioate was recovered (90% mass recovery). Using chiral HPLC as described in the specification showed an e.r. of 99.2:0.8. Photomicrograph analysis of salts showed both isomers to be crystalline. NMR analysis of the salts confirms a 1:1 adduct of substrate to resolving agent.

EXAMPLE 8

Salt Resolution of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one Using (S)-(−)-1,1'-binapthyl-2,2'-diyl hydrogenphosphate 200 mg of racemic 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one was combined with 80–140 mg of (S)-(−)-1,1'-binapthyl-2,2'-diyl hydrogenphosphate (S-BINAP). The solids were diluted with 3–5 ml of either 10% acetone: 90% ethyl acetate or 20% acetone: 80% ethyl acetate. The mixture was stirred at 60° C. for 16 hours. The solids were filtered and dried in vacuo for 16 hours at 40° C. to recover (+)-6-[(4-chloro-phenyl)-hydroxy-(3-methyl-3H-imidazol -4-yl)-methyl]-4-[3-(3-hydroxy-3-methyl-but-1-ynyl)-phenyl]-1-methyl-1H-quinolin-2-one, (−)-1,1'-binapthyl-2,2'-diyl hydrogenphosphate. The solids were then recombined of either 10% acetone: 90% ethyl acetate or 20% acetone: 80% ethyl acetate and stirred at 60° C. for 16 hours. The solids were filtered and dried as before. The repulps were continued until the desired chiral purity was achieved.

The following table shows the weight recoveries and chiral purities for (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (−)-1,1'-binapthyl-2,2'-diyl hydrogenphosphate following repeated repulping using the process described above.

phase comprising a derivatized polysaccharide that is selected from the amylosic and cellulosic class of polysaccharides, and recovering the enantiomerically pure of optically enriched 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one.

|  | Salt Formation | Repulp 1 | Repulp 2 | Repulp 3 | Repulp 4 | Solvent | Overall Yield |
|---|---|---|---|---|---|---|---|
| Yield | 115.60% | 81.40% | 86.50% | 90% | 82.30% | 10%:90% Acetone:EtOAc | 60.30% |
| Chiral Purity | 68.50% | 83.00% | 89.60% | 92.20% | 94.00% | | |
| Yield | 95.60% | 77.40% | 57.20% | 88% | 89.60% | 20%:80% Acetone:EtOAc | 33.70% |
| Chiral Purity | 73.90% | 89.10% | 94.60% | 95.90% | 96.60% | | |

It should be understood that the invention is not limited to the particular embodiments described herein, but that various changes and modification may be made without departing from the spirit and scope of this novel concept as defined by the following claims.

What is claimed is:

1. A process for chromatographically resolving 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one using continuous chromatography, the continuous chromatography comprising contacting a mixture containing 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, liquid mobile phase comprising at least one polar solvent and a solid chiral stationary phase comprising a derivatized polysaccharide that is selected from the amylosic and cellulosic class of polysaccharides and recovering the chromatographically resolved 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one.

2. The process according to claim 1, wherein the chromatographic method employed is a selected from the group consisting of simulated moving bed chromatography, high performance liquid chromatograph and cyclojet process.

3. The process according to claim 2, wherein the chromatographic method is simulated moving bed chromatography.

4. The process according to claim 2, wherein the chromatographic method is high performance liquid chromatograph.

5. The process according to claim 4, wherein the solid chiral stationary phase is an amylosic polysaccharide.

6. The process according to claim 5, wherein the solid chiral stationary phase is selected from amylose 3,4-substituted phenyl carbamate, cellulose 3,5-substituted phenyl carbamate or cellulose 4-substituted benzoate.

7. The process according to claim 6, wherein the chiral stationary phase is an analog of amylose tris (3,5-substituted phenyl carbamate) wherein the substituent is 3,5-dimethyl.

8. A process for the production of enantiomerically pure or optically enriched 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one using simulated moving bed chromatography, the moving bed chromatography comprising contacting a mixture containing 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, a liquid mobile phase comprising at least one polar solvent and a solid chiral stationary 9. The process of claim 8, wherein the chiral stationary phase is selected from amylose 3, 4-substituted phenyl carbamate, cellulose 3,5-substituted phenyl carbamate or cellulose 4-substituted benzoate.

10. The process of claim 9, wherein the chiral stationary phase is an analog of amylose tris (3,5-substituted phenyl carbamate) wherein the substituent is 3,5-dimethyl.

11. The process of claim 9, wherein the chiral stationary phase is a cellulose 3,5-substituted phenyl carbamate or cellulose 4-substituted benzoate polysaccharide analog.

12. The process of claim 9, wherein the mobile phase comprises a solvent that is selected from heptane, hexane, isopropanol, ethanol, methanol, methyl acetate, acetonitrile, methylene chloride, ethyl acetate and/or mixtures thereof.

13. The process of claim 12, wherein the mobile phase is selected from heptane and ethanol or isopropanol and/or a mixture of methanol and ethanol with or without heptane.

14. The process of claim 1, wherein the polysaccharide derivative is immobilized on silica gel, zirconium, alumina, ceramics and other silicas.

15. The process of claim 1, using an amylose 3,4-substituted phenyl carbamate derivative polysaccharide analog with a mobile phase of a mixture of heptane and ethanol or methanol and ethanol.

16. The process of claim 11, using an amylose tris (3,5-substituted phenyl carbamate) with a mobile phase of a mixture of heptane and ethanol.

17. The process of claim 12, using an amylose tris (3,5-substituted phenyl carbamate) with a mobile phase of mixture of ethanol and methanol wherein the percentage of ethanol and methanol are 1:1 (v/v).

18. The process of claim 1, wherein retention times are increased or decreased by varying the mobile phase components.

19. The process of claim 1, wherein said separation affords at least one of the enantiomers a recovery of greater than or equal to 90%.

20. The process of claim 1, using a temperature range of about 5 to 45° C.

21. The process of claim 20, using a temperature range of about 20 to 40° C.

22. The process of claim 1, wherein the separation factor α is about 1.2 to 5.0

23. The process of claim 22, wherein using a temperature of about 25° C. takes advantage of increased solubility of 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one in the mobile phase.

24. A process for preparing (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, L-(+)-tartaric acid comprising treating 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one with L-(+)-tartaric acid.

25. The process of claim 24, wherein said process is carried out in a mixture of propanol and water.

26. The process of claim 25, wherein optically enriched (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, L-(+)-tartrate seed is added to the mixture.

27. The process of claim 26, wherein said mixture is cooled and crystallized.

28. The process of claim 25, wherein said propanol is 2-propanol.

29. A process for preparing (+)-6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one, (S)-(−)-1,1'-binapthyl-2,2'-diyl hydrogenphosphate comprising treating 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one with (S)-(−)-1,1'-binapthyl-2,2'-diyl hydrogenphosphate.

30. The process of claim 29, wherein said process is carried out in a mixture of acetone and ethyl acetate.

31. The process of claim 30, wherein solids were filtered and dried in vacuo.

32. The process of claim 31, wherein said dried solids are recombined with acetone and ethyl acetate.

33. The process of claim 32, wherein said mixture is stirred for 1 to 24 hours.

34. The process of claim 33, wherein said mixture is filtered to isolate solids.

35. The process of claim 34, wherein said solids are dried in vacuo.

* * * * *